United States Patent
Mangino et al.

(10) Patent No.: US 12,337,012 B2
(45) Date of Patent: *Jun. 24, 2025

(54) COMPOSITIONS AND METHODS FOR RESTORING OR INCREASING TISSUE PERFUSION

(71) Applicant: VIRGINIA COMMONWEALTH UNIVERSITY, Richmond, VA (US)

(72) Inventors: Martin J. Mangino, Richmond, VA (US); Loren K. Liebrecht, Richmond, VA (US)

(73) Assignee: Virginia Commonwealth University, Richmond, VA (US)

( * ) Notice: Subject to any disclaimer, the term of this patent is extended or adjusted under 35 U.S.C. 154(b) by 652 days.

This patent is subject to a terminal disclaimer.

(21) Appl. No.: 17/761,792

(22) PCT Filed: Sep. 23, 2020

(86) PCT No.: PCT/US2020/052075
§ 371 (c)(1),
(2) Date: Mar. 18, 2022

(87) PCT Pub. No.: WO2021/061687
PCT Pub. Date: Apr. 1, 2021

(65) Prior Publication Data
US 2022/0387478 A1 Dec. 8, 2022

Related U.S. Application Data

(60) Provisional application No. 62/907,066, filed on Sep. 27, 2019.

(30) Foreign Application Priority Data

Mar. 27, 2020 (WO) ................ PCT/US2020/025103

(51) Int. Cl.
*A61K 31/765* (2006.01)
*A61K 9/08* (2006.01)
*A61K 47/08* (2006.01)

(52) U.S. Cl.
CPC .............. *A61K 31/765* (2013.01); *A61K 9/08* (2013.01); *A61K 47/08* (2013.01)

(58) Field of Classification Search
None
See application file for complete search history.

(56) References Cited

U.S. PATENT DOCUMENTS

2014/0100289 A1 4/2014 Shi et al.
2016/0104218 A1 4/2016 O'Donnell et al.
(Continued)

FOREIGN PATENT DOCUMENTS

CN 103492016 A * 1/2014 ......... A61K 49/0004
JP 2011500779 A 1/2011
(Continued)

OTHER PUBLICATIONS

CN103492016A—English translation (Year: 2014).*
Napolitano, Resuscitation endpoints in trauma, Transfusion Alternatives in Transfusion medicine, vol. 6, No. 4, Mar. 2005.

*Primary Examiner* — Kyung S Chang
(74) *Attorney, Agent, or Firm* — WCF IP (57) ABSTRACT

A composition for restoring or increasing tissue perfusion is provided. The composition includes polyethylene glycol polymers (PEG) with a molecular weight of 18,000-100,000 Da at a concentration of 5-20% by weight; PEG with a molecular weight of 1,000-10,000 Da at a concentration of 1-30% by weight; and water, wherein said PEG with a molecular weight of 18,000-100,000 Da and said PEG with a molecular weight of 1,000-10,000 Da are dissolved or dispersed in said water.

19 Claims, 7 Drawing Sheets

(56) References Cited

U.S. PATENT DOCUMENTS

2017/0151198 A1    6/2017   Mangino
2018/0104218 A1    4/2018   Beilman

FOREIGN PATENT DOCUMENTS

| JP | 2012519692 A | 8/2012 |
| WO | 1999008514 A1 | 2/1999 |
| WO | 2009053741 A2 | 4/2009 |
| WO | 2010101971 A1 | 9/2010 |

* cited by examiner

COMPOSITIONS AND METHODS FOR RESTORING OR INCREASING TISSUE PERFUSION

STATEMENT REGARDING FEDERALLY SPONSORED RESEARCH OR DEVELOPMENT

This invention was made with government support under Grant Number W81XWH-16-2-0040 awarded by the Department of the Army/MRMC. The government has certain rights in the invention.

FIELD OF THE INVENTION

The invention is generally related to compositions comprising high and low molecular weight polymer agents useful for restoring or increasing oxygen delivery to the microcirculation in ischemic tissues.

BACKGROUND

Resuscitation of trauma and shock patients with whole blood or blood products is considered the gold standard of fluid resuscitation. However, there are certain mechanisms of cell and tissue injury during shock that severely limits the effectiveness of any solution used to resuscitate shocked patients. While whole blood may be the best option when compared to other IV solutions like lactated ringers solution, it too is severely disadvantaged by the no-reflow phenomenon that occurs when ischemic tissues are reperfused.

Improved compositions and methods that alleviate this mechanism of tissue injury to allow the whole blood to easily pass through the capillary network in vital organs and tissue so the needed oxygen transfer can occur is needed in order to alleviate and reverse the metabolic effects of shock.

SUMMARY

The present disclosure provides a safe and inert solution that is used to resuscitate trauma or shocked patients, for example, in the hospital or emergency department. The solution greatly improves the oxygen transfer to the patient's tissues, improves post-resuscitation outcomes, and increases patient survival. When the solution is administered prior to a blood transfusion, it reduces the amount of blood needed for the transfusion.

An aspect of the present disclosure provides a composition comprising polyethylene glycol polymers (PEG) with a molecular weight of 18,000-100,000 Da at a concentration of 5-20% w/v; PEG with a molecular weight of 1,000-10,000 Da at a concentration of 1-30% w/v; and water, wherein said PEG with a molecular weight of 18,000-100,000 Da and said PEG with a molecular weight of 1,000-10,000 Da are dissolved or dispersed in said water. In some embodiments, the total volume of the composition is 1000 ml or less, e.g. 100-1000 ml. In some embodiments, the total volume ranges from 136-680 ml.

In some embodiments, the composition comprises PEG with a molecular weight of 20,000 Da at a concentration of 10% w/v. In some embodiments, the composition comprises PEG with a molecular weight of 1,000 Da at a concentration of 15% w/v. In some embodiments, the water is deionized water. In some embodiments, the composition further comprises one or more of sodium chloride, sodium lactate, potassium chloride, calcium chloride, and magnesium chloride.

Another aspect of the disclosure provides an intravenous infusion product, comprising a bag configured for delivering fluid intravenously and a composition as described herein within the bag.

Another aspect of the disclosure provides a method for restoring or increasing local or global tissue perfusion in a subject in need thereof, comprising administering to the subject a therapeutically effective amount of a composition as described herein. In some embodiments, the composition is administered intraveneously. In some embodiments, the subject suffers from reduced global or local tissue perfusion due to cardiogenic or noncardiogenic shock.

In some embodiments, the method comprises a step of simultaneously or sequentially administering a cellular or acellular oxygen carrier solution. In some embodiments, the acellular oxygen carrier solution is a hemoglobin based oxygen carrier (HBOC). In some embodiments, the cellular oxygen carrier solution is whole blood or packed red blood cells. In some embodiments, the amount of the cellular oxygen carrier solution administered is 50% or less of the estimated blood volume that would otherwise be needed in the absence of the composition. In some embodiments, the cellular or acellular oxygen carrier solution is administered within 12 hours of administering the composition.

DETAILED DESCRIPTION

Embodiments of the disclosure provide a solution that restores or increases oxygen delivery to the microcirculation in ischemic tissues. The ischemia may result from noncardiogenic (e.g. hypovolemic, obstructive, septic, anaphylactiv, or neurogenic) shock or cardiogenic shock. The composition described herein targets a novel mechanism of action that is a major causal factor in poor tissue perfusion that occurs during ischemia and after reperfusion-resuscitation, specifically, metabolic cell swelling and secondary microcirculatory compression.

Figure 1A:
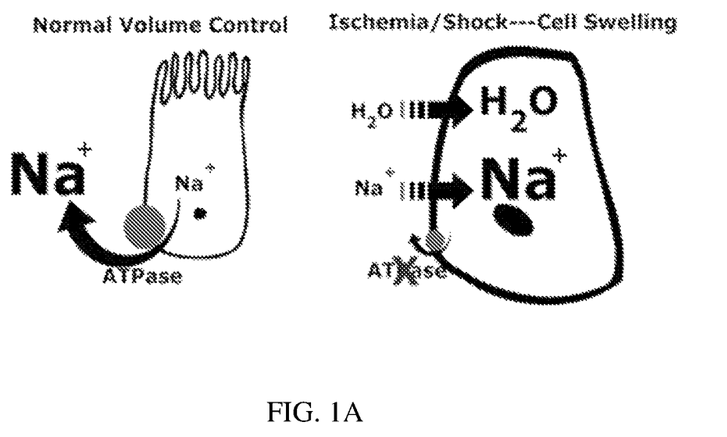
FIGS. 1A-B. (A) Illustration of osmotic water movement and metabolic cell swelling during shock. (B) Illustration of metabolic cell swelling of endothelial cells and associated capillary compression.
Figure 1B:
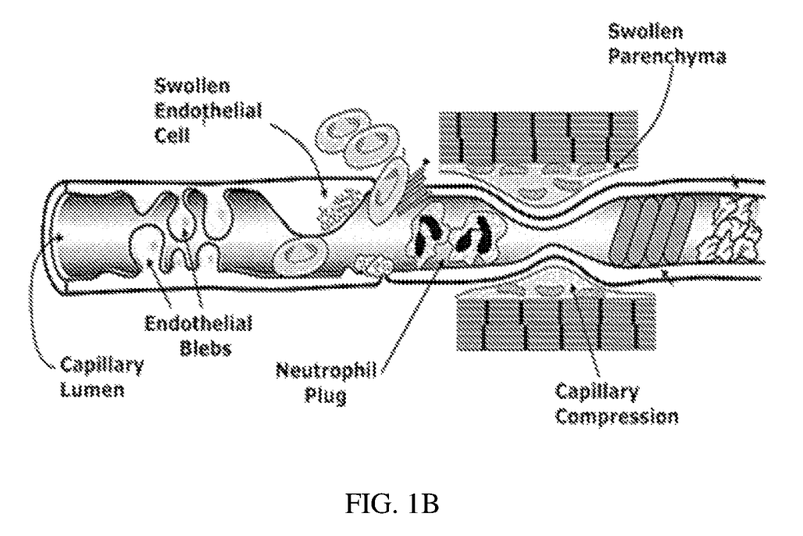

Cell ischemia that occurs during shock results in loss of ATP concentrations necessary to run the Na/K ATPase in the basolateral plasma membrane. This causes slowing of the sodium pump resulting in increased entry of sodium into the cell and subsequent osmotic water movement resulting in metabolic cell swelling (FIG. 1A). As parenchymal cells in tissues swell, the microcirculation supplying oxygen to the tissues compresses and slows or stops capillary flow and convective transfer of oxygen. Similarly, metabolic swelling of endothelial cells reduces the diameter of the capillary lumen further restricting flow (FIG. 1B). This can be prevented or reversed by loading the extracellular space with cell impermeants which are inert molecules that escape the capillary space but cannot enter the cell. They accumulate outside the cell and osmotically prevent or reverse inward water movement, thereby preventing tissue edema and decompressing the microcirculation. This results in efficient capillary perfusion and transfer of oxygen into the tissues even during low volume states.

Figure 2:
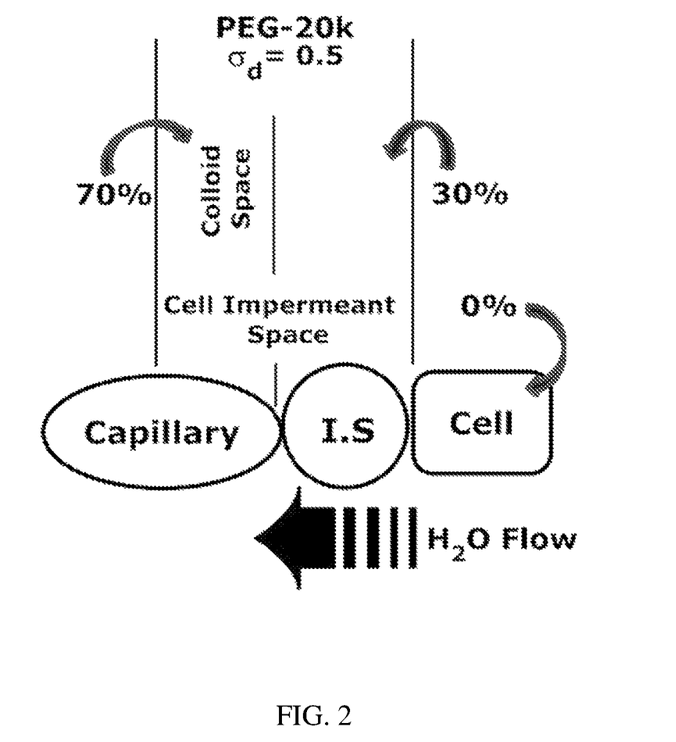
FIG. 2. Illustration of osmotic gradients that result in non-energetic transfer of isotonic water out of the cell and into the capillary.

Polyethylene glycol (PEG) polymers with a molecular weight of about 18,000-100,000 Da are most effective because of two phenomena: 1) they are impermeant molecules with partial oncotic properties, and 2) they are highly hydrophilic and attract water molecules. Tracer studies suggest that the osmotic reflection coefficient ($\sigma d$) of PEG-20k molecules is about 0.5, which means that for every 2 molecules of PEG-20k that stays in the capillary space, 1 exits and enters the interstitial space. None get into the cell because it is an impermeant. This creates the osmotic gradients to establish non-energetic transfer of isotonic water out of the cell and into the capillary (see FIG. 2). This water transfer promotes decompression of the capillary bed that decrease resistance to flow while reloading the capillaries with volume to enhance driving pressure for flow. PEG polymers are extremely hydrophilic and avidly attract water shells around the molecule. This potentiates the water pull over just the osmotic gradients.

Low flow states and pro-inflammatory states that occur in shock, trauma, critical illness, and tissue injury cause slow flow through ever decreasing numbers of capillaries in the tissues (poor perfusion). One mechanism for this includes the formation of red blood cell (RBC) rouleaux, which are the stacking together of columns of RBCs in the microcirculation. These RBC rouleaux trap in the capillaries and impede flow by physical obstruction, increase local blood viscosity, and cross-linking with other inflammatory cells adhered to the injured vascular endothelium and by glycocalyx disruption in shock. Therapeutic PEG polymers (from 20-100k) increase RBC aggregation and are more likely to enhance rouleaux formation in shock and low flow states. This works against the protective effects produced by these therapeutic PEG polymers to restore capillary flow and perfusion by limiting metabolic cell and tissue swelling.

The present disclosure provides compositions comprising the therapeutic PEG polymers combined with small amounts of low molecular weight blockers to enhance the therapeutic effects on local capillary perfusion by limiting rouleaux formation. Thus, embodiments of the disclosure provide a composition comprising PEG with a molecular weight of 18,000-100,000 Da, e.g. 18,000-40,000 Da, e.g. 20,000-35,000 Da, e.g. 18,000 Da, 20,000 Da, 25,000 Da, 30,000 Da, 35,000 Da, or 40,000 Da at a concentration of 5-30% by weight, e.g. 5-20%, 10-30%, or 10-20% w/v, g/L total solution. The composition further comprises PEG with a molecular weight of 1,000-10,000, e.g. 2,000-8,000 Da, e.g. 2,000, 3,000, 4,000, 5,000, 6,000, 7,000 or 8,000 Da, e.g. 6,000 Da at a concentration of 1-30%, e.g. 1-20% or 1-10% w/v, g/L total solution.

Most PEGs include molecules with a distribution of molecular weights (i.e. they are polydisperse). The size distribution can be characterized statistically by its weigh average molecular weight (Mw) and its number average molecular weight (Mn), the ratio of which is called the polydispersity index (Mw/Mn). In some embodiments, the polydispersity index is less than about 5, e.g. less than 4, 3, 2, 1.5, or 1.2.

The smaller polymers provide two important actions: 1) they attenuate the large PEG molecule enhanced rate of erythrocyte sedimentation either in vivo when administered separately from whole blood or blood product or in vitro when provided as a combined blood product, making the product easier to administer, and 2) they provide short-term immuno-camouflage of activated components of the cellular immune system after resuscitation, thereby blocking some of the early pro-inflammatory responses after resuscitation Immuno-camouflage is accomplished by a non-specific surface passivation of the blood cells by the polymers. The polymers cover activated surface receptors for cell-cell interactions and thus further protect against secondary inflammation injury after resuscitation by "coating" white blood cells to cloak or camouflage them from activation by injured tissues.

The high and low molecular weight PEG are dissolved or dispersed in water, e.g. deionized water. In some embodiments, the composition is a saline or lactate ringer's solution and comprises one or more of sodium chloride, sodium lactate, potassium chloride, calcium chloride, and magnesium chloride.

In some embodiments, the total volume of the composition is 1000 ml or less, e.g. 500 ml, 250 ml, or 150 ml or less, e.g. 100-1000 ml. In some embodiments, the total volume ranges from about 136-680 ml based on a dose of 6.8 ml/kg body weight for patients from 20-100 kg.

The solution may be a single phase solution, a dispersion, an emulsion, or any other form physically suitable for delivery to the subject. The solution is "physiologically acceptable" in that it is suitable for injection into the subject without causing undue deleterious effects. The solution may comprise autologous blood or a blood substitute. In some embodiments, the solution comprises additional cell impermeants or oncotic agents.

Figure 7:
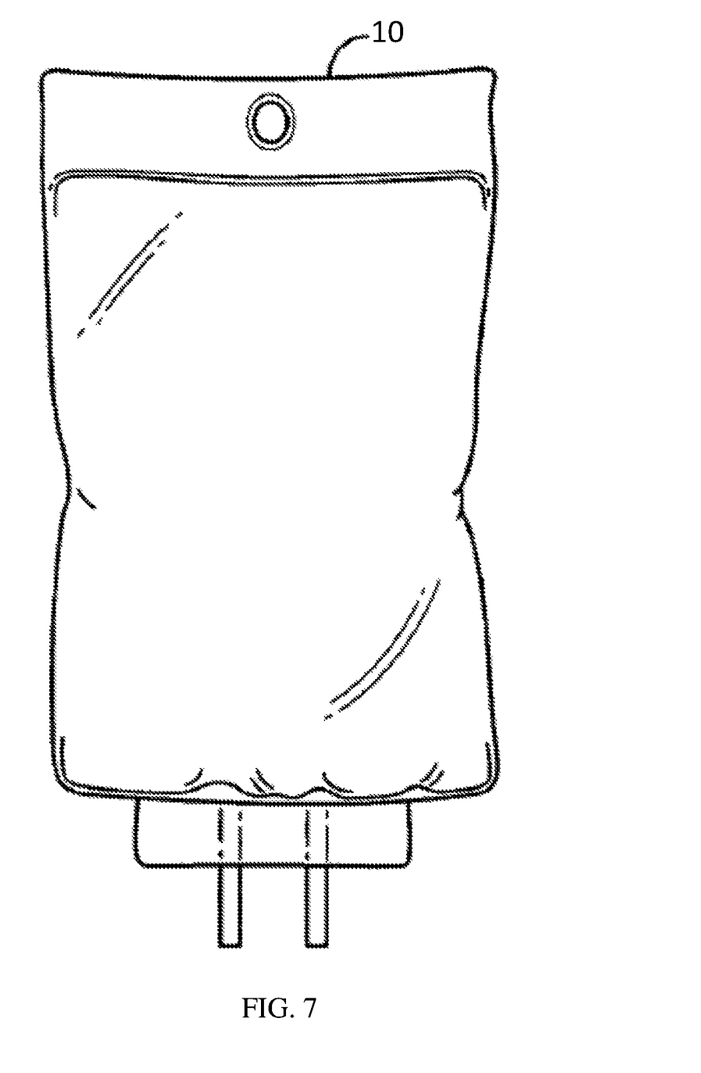
FIG. 7. An intravenous infusion product according to some embodiments of the disclosure.

With reference to FIG. 7, further embodiments of the disclosure provide an intravenous infusion product comprising a bag 10 configured for delivering fluid intravenously and a composition as described herein within the bag. Suitable IV infusion bags, such as Viaflex® bags, are well known in the art.

Further embodiments of the disclosure provide a composition as described herein mixed with a cellular or acellular oxygen carrier solution. Acellular oxygen carrier solutions include hemoglobin based oxygen carriers (HBOC) such as Hemopure®, emulsions of perfluorochemical liquids (PEC emulsions) and lipid encapsulation of either of these oxygen carriers. Cellular oxygen carriers include whole blood, e.g. administered via a blood transfusion or packed red blood cells. Thus, the composition described herein may be a sterile additive for whole blood or blood products or other oxygen carrier solutions that is used to resuscitate patients with trauma, hypovolemia, shock, or metabolic extremis secondary to poor perfusion. The additive may be combined with a unit of whole blood or added to donor bags at the time of whole blood collection. For example, the 50-150 ml of the composition may be filter sterilized and mixed with 400-600 ml of acid-citrase-dextrose (ACD) treated whole blood. The combined product dramatically increases the effectiveness of whole blood resuscitation and increases patient outcomes and survival.

Further embodiments provide methods for restoring or increasing local or global tissue perfusion in a subject in need thereof, e.g. a trauma or shock patient, comprising administering to the subject a therapeutically effective amount of a composition as described herein. The composition may be added simultaneously with or prior to administration of a cellular or acellular oxygen carrier solution. In some embodiments, the cellular or acellular oxygen carrier solution is administered within 12 hours, e.g. within 10, 8, 6, 4, 2, or 1 hour, of administering the composition. In some embodiments, the amount of the cellular oxygen carrier solution administered is 50% or less, e.g. 40%, 30%, 20%, 10%, or 5% or less, of the estimated blood volume that would otherwise be needed in the absence of the composition.

Further embodiments provide methods for resuscitation of the heart in a subject in need thereof, e.g. a trauma or shock patient, comprising administering to the subject a therapeutically effective amount of a composition as described herein. The composition may be added simultaneously with or prior to administration of a cellular or acellular oxygen carrier solution. In some embodiments, the cellular or acellular oxygen carrier solution is administered within 12 hours, e.g. within 10, 8, 6, 4, 2, or 1 hour, of administering the composition. In some embodiments, the amount of the cellular oxygen carrier solution administered is 50% or less, e.g. 40%, 30%, 20%, 10%, or 5% or less, of the estimated blood volume that would otherwise be needed in the absence of the composition.

The solution described herein may be administered by any suitable means such as via intra-arterial, intravenous, intraosseous, or intracardiac routes.

The term "subject" or "patient" generally refers to any mammal, typically humans The solutions and methods described herein also have veterinary applications including, but not limited to, companion animals and farm animals.

As used herein, the terms "effective amount," or "therapeutically effective amount" refer to a nontoxic but sufficient amount of an agent to provide the desired biological result. That result may be reduction and/or alleviation of the signs, symptoms, or causes of a disease, or any other desired alteration of a biological system, such as the reduction or inhibition of metabolic cell and tissue swelling during resuscitation.

The compositions described herein allow blood to easily pass through the capillary network in vital organs and tissue so the needed oxygen transfer can occur to alleviate and reverse the metabolic effects of shock. The compositions described herein may be administered to critically ill patients that have suffered global oxygen debt (a plasma lactate over 2.5 mM). The composition improves performance of the whole blood or blood product administered simultaneously or sequentially in terms of oxygen delivery and transfer of oxygen to hypoxic tissues with added protections against overt cellular inflammation as a secondary injury. The composition improves outcomes and survival, relative to the same volume of whole blood or blood product without the composition.

The compositions described herein solve the "no reflow" problem with fluid resuscitation, which is far more significant than previously appreciated. Administration of whole blood to shocked patients does no good if the blood cannot reach the capillary exchange vessels (capillary no reflow). Fixing "no reflow" allows the oxygen carrying whole blood to move into capillary spaces to affect much needed oxygen transfer to ischemic tissue. This drives down lactates, pays back the incurred oxygen debt, and dramatically increases survival.

The compositions described herein are useful for hospital transfusions for patients with metabolic and cardiovascular distress (e.g. as indexed by a plasma lactate greater than 2.5 mM). Other uses include for critically ill patients in the surgical or medical ICU, burn patients, trauma patients at risk for compartment syndrome, transplant patients receiving a graft, organ donors with cardiovascular collapse, operating room use for treating rapid blood loss, and transport use when there is blood loss or cardiovascular collapse. The product may also be used in forward field hospitals in military conflict zones, in transport vehicles on the ground and in the air, and anywhere there is a need for whole blood in patients suffering from some form of oxygen deprivation from cardiovascular collapse, shock, trauma, or illness.

Before exemplary embodiments of the present invention are described in greater detail, it is to be understood that this invention is not limited to particular embodiments described, as such may, of course, vary. It is also to be understood that the terminology used herein is for the purpose of describing particular embodiments only, and is not intended to be limiting, since the scope of the present invention will be limited only by the appended claims.

Where a range of values is provided, it is understood that each intervening value, to the tenth of the unit of the lower limit unless the context clearly dictates otherwise, between the upper and lower limit of that range and any other stated or intervening value in that stated range, is encompassed within the invention. The upper and lower limits of these smaller ranges may independently be included in the smaller ranges and are also encompassed within the invention, subject to any specifically excluded limit in the stated range. Where the stated range includes one or both of the limits, ranges excluding either or both of those included limits are also included in the invention.

Unless defined otherwise, all technical and scientific terms used herein have the same meaning as commonly understood by one of ordinary skill in the art to which this invention belongs. Although any methods and materials similar or equivalent to those described herein can also be used in the practice or testing of the present invention, representative illustrative methods and materials are now described.

All publications and patents cited in this specification are herein incorporated by reference as if each individual publication or patent were specifically and individually indicated to be incorporated by reference and are incorporated herein by reference to disclose and describe the methods and/or materials in connection with which the publications are cited. The citation of any publication is for its disclosure prior to the filing date and should not be construed as an admission that the present invention is not entitled to antedate such publication by virtue of prior invention. Further, the dates of publication provided may be different from the actual publication dates which may need to be independently confirmed.

It is noted that, as used herein and in the appended claims, the singular forms "a", "an", and "the" include plural referents unless the context clearly dictates otherwise. It is further noted that the claims may be drafted to exclude any optional element. As such, this statement is intended to serve as antecedent basis for use of such exclusive terminology as "solely," "only" and the like in connection with the recitation of claim elements, or use of a "negative" limitation.

As will be apparent to those of skill in the art upon reading this disclosure, each of the individual embodiments described and illustrated herein has discrete components and features which may be readily separated from or combined with the features of any of the other several embodiments without departing from the scope or spirit of the present invention. Any recited method can be carried out in the order of events recited or in any other order which is logically possible.

The invention is further described by the following non-limiting examples which further illustrate the invention, and are not intended, nor should they be interpreted to, limit the scope of the invention.

Example 1

PEG Polymer Size for Hemorrhagic Shock Resuscitation

Figure 3A:
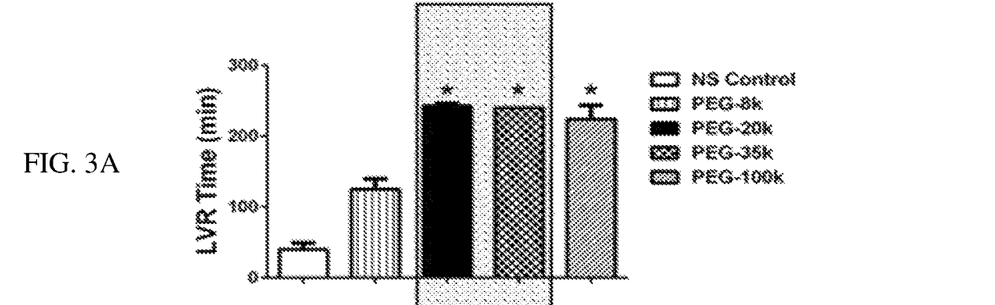
FIGS. 3A-C. (A) LVR time, (B) Terminal lactase, and (C) Terminal MAP after administration of various LVR solutions.
Figure 3B:
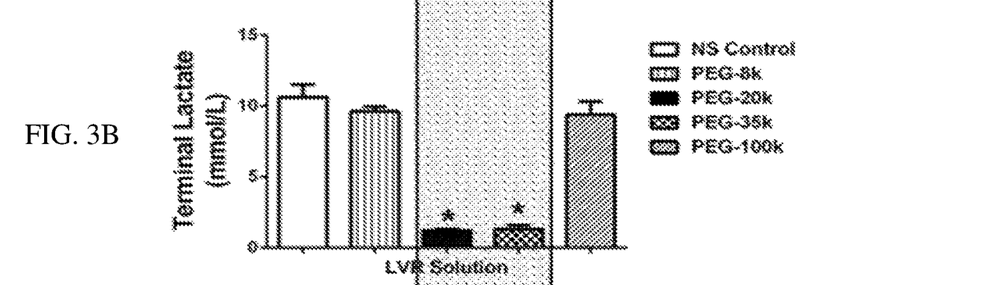
Figure 3C:
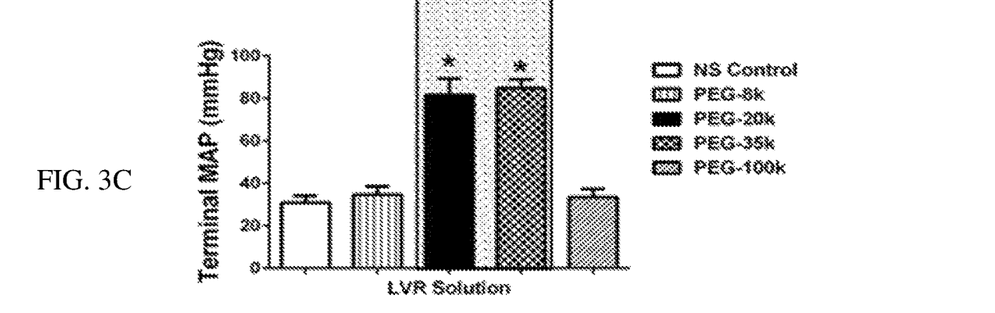

Early studies in a robust rodent model of lethal hemorrhagic shock and low volume resuscitation (LVR) indicated classic impermeant molecules were highly effective because they doubled the low volume resuscitation (LVR) time, which is an index of tolerance to shock. Other cardiovascular and metabolic outcomes were also improved two-fold, relative to the saline volume control group. To optimize the effects, we searched for impermeant molecules with osmotic reflection coefficients less than 1 (a pure oncotic agent like albumin that stays in the capillary space) and greater than 0 (a pure impermeant like gluconate that freely equilibrates between the capillary and interstitial space). We found polymers of PEG greater than 10k but less than 100k were attractive candidates. Sizing studies in shock were conducted where the outcomes were LVR time, arterial pressure after resuscitation, and plasma lactate accumulation after resuscitation as an index of oxygen debt. These studies are summarized in FIG. 3.

Results indicate that PEG-8k produced a 2-3 fold increase in shock tolerance, similar to gluconate and consistent with its molecular reflection coefficient. PEG polymers between 20-35k produced optimal results in the rodent shock model since they had the highest LVR time, highest terminal mean arterial pressures, and lowest end lactate values. In fact, PEG-20k and -35k caused lactate to fall from 10 mM at resuscitation to near baseline (1.2 mM), which indicates a repayment of oxygen debt in 4 hours. Low volume resuscitation with PEG-100k produced good results, based on LVR times but the rats were beginning to deteriorate since their MAP was very low (around 40 mmHg 4 hours after resuscitation) and their lactate rose back up to near 10 mM, suggesting they were re-accumulating oxygen debt. Therefore, it appears that PEG polymer sizes between 20-35 kDa are optimal for resuscitation after lethal shock.

Example 2

PEG Dose for Hemorrhagic Shock Resuscitation

Figure 4:
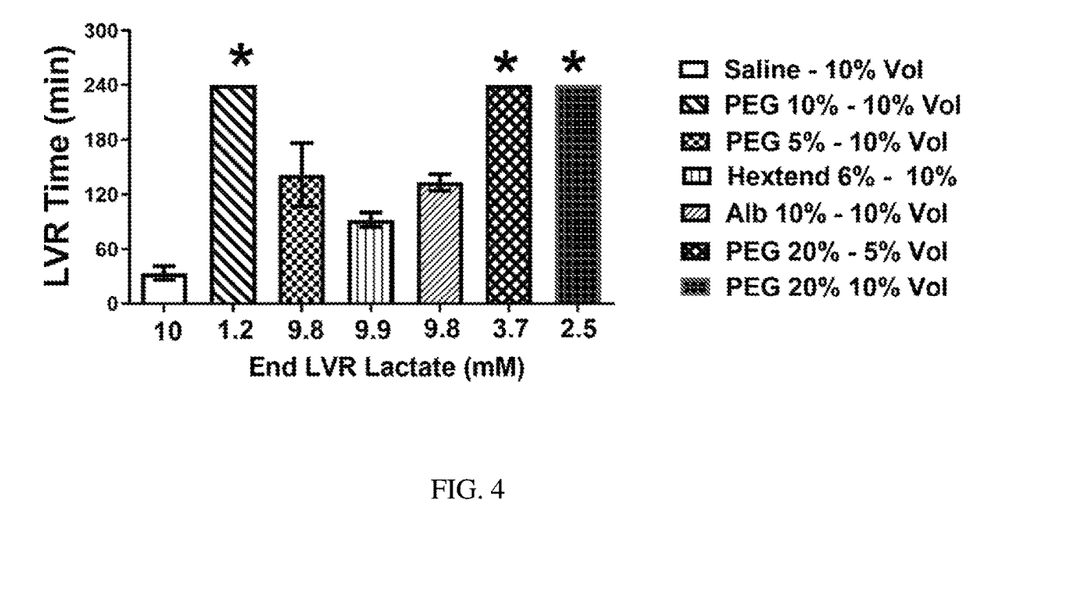
FIG. 4. Dose response data in a rodent model of lethal shock.

The current dose recommended for shock resuscitation is a single low volume IV bolus infusion of a volume equal to 10% of the estimated blood volume or 6.8 ml/kg. The solution used is a 10% weight to volume solution of polyethylene glycol 20,000 (PEG-20k). The dose is administered over 5 minutes by an infuser or by gravity feed to a venous access line. This specific dosage was determined empirically from iterative experimentation in a well-developed rodent model of lethal shock that was shown to correlate with the preclinical swine model. These dose response data are shown in FIG. 4. These data show optimum doses of PEG-20k IV solution based on both LVR times and end plasma lactate outcomes. Specifically, the most effective resuscitation outcome is the one with the longest LVR time and the lowest end lactate (shown under each bar in mM/L). Using these criteria in this testing model, PEG-20k IV administered as a 10% solution of PEG-20k at a volume dose of 10% of the estimated blood volume (6.8 ml/kg) produced the clearest optimal results.

Reducing the concentration to 5% (at a 10% EBV dose) or the dose to 5% EBV with a 10% solution produced inferior outcomes. Similarly, delivering the same mass of PEG-20k but in half the volume (20% solution delivered in a 5% EBV dose) was inferior, suggesting that the same effective mass of PEG-20k requires a minimal volume of isotonic vehicle (Lactated Ringers solution component). This makes sense since the mechanism is to move isotonic volume out of the cells and to reload the capillary spaces. A minimal replacement fluid volume of 10% EBV (6.8 ml/kg) is required. This falls within the upper limits of what is still considered a low volume resuscitation volume. While a 10% PEG-20k solution produced optimal results, doubling the concentration was not more effective and was less beneficial since the end lactate concentrations were slightly higher at the end of the 240 minute LVR period (1.2 mM Vs 2.5 mM for 10% PEG-20k compared to 20% PEG-20k, respectively). The optimal PEG-20k dose is also compared to the performance of other common crystalloids that may be used as LVR solutions in shock resuscitation (Saline, Hextend, and Albumin) In other studies, resuscitation with a solution containing 7.5% PEG-20k was not significantly different from the 10% solution.

Example 3

Formulation Optimization: The ESR Effect

Figure 5:
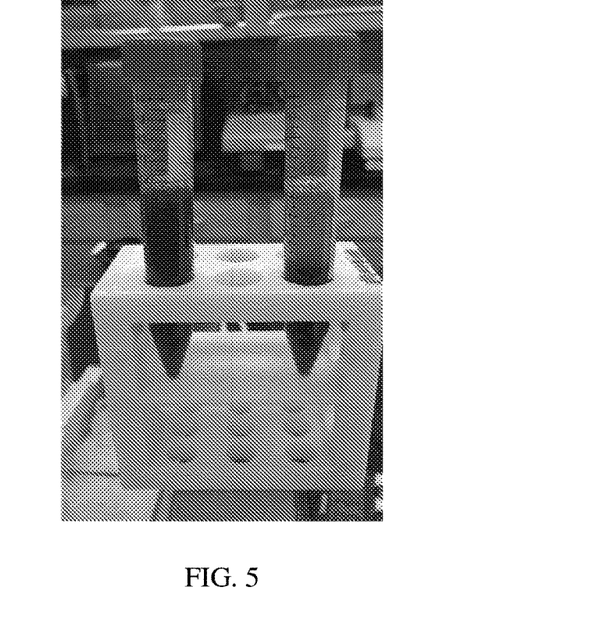
FIG. 5. Red blood cell sedimentation after addition of 10% PEG-20k to whole human blood.

Large polymer sizes of PEG that have these salutary effects on resuscitation after severe shock also dramatically increase the red blood cell sedimentation rate (ESR) when mixed with whole blood. Polyethylene glycol polymers can non-specifically bind to biological and non-biological materials. Furthermore, polymers with a molecular radius of >4 nM can bind and cross link cells such as red blood cells while polymers <4 nM do not. This translates into a molecular weight cut-off between 10-20 kDa, such that PEG-20k is large enough to interact with RBCs and PEG-10k in size and less is not. One of the first observations we made when working with 10% PEG-20k IV solutions in vivo in preclinical models of shock was the ability to cause the RBCs in whole blood samples taken after IV administration of a single dose of PEG-20k to rapidly settle out of solution (FIG. 5—right side—contains 10% solution of PEG-20k. The picture shows the degree of red blood cell sedimentation after only 10 minutes). Quantitating this effect using the classic Westergren ESR test in ex-vivo human blood was used to quantitate the PEG-20k ESR effect. Sedimentation in normal blood at 60 mM was about 2-6 mm. This increased to 60 mm when the blood was diluted with 10% PEG-20k at a 1:9 dilution, which simulates the dilution after LVR in shock.

We next measured ESR rates using a standard Westergren ESR assay and tried to block or attenuate the sedimentation effect by adding a family of different concentrations of smaller PEG polymers that would act as competitive inhibitors of the binding sites on the RBCs. Without being bound by theory, our hypothesis is that the larger PEG polymers nonspecifically bind to RBC charged surfaces. When multiple RBCs attach to each large polymer, then cross linking occurs that increases the blood particle density, which causes them to settle out of solution quickly. We hypothesized that smaller polymers would have the same affinity for the surface of the RBC but not be able to accommodate multiple RBC binding and therefore, not allow for cross linking.

Figure 6A:
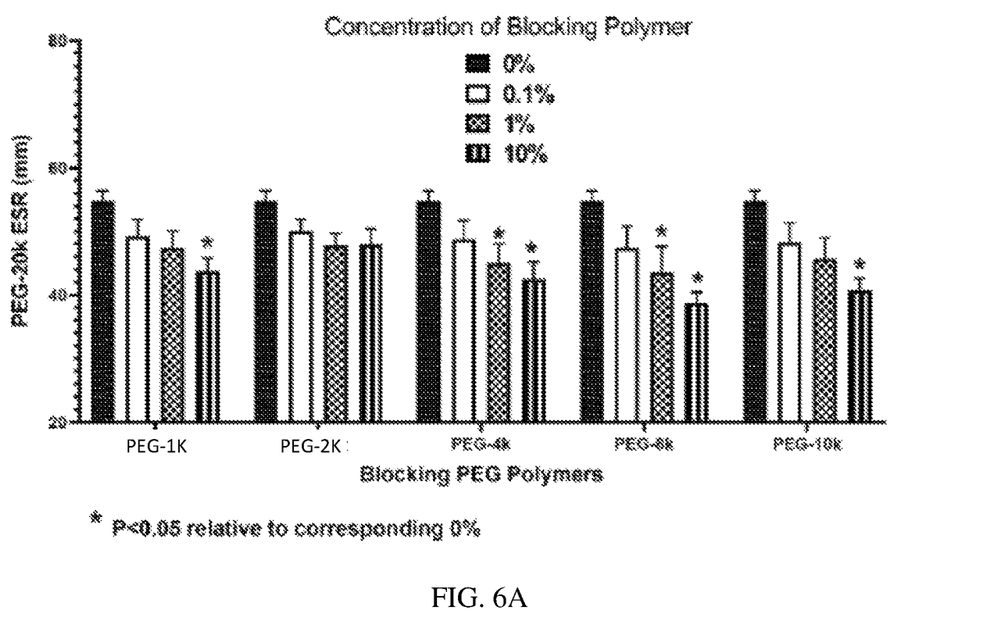
FIGS. 6A-C. Westergren ESR assay data describing the effects of small molecule PEG polymers on the larger polymer (A) PEG-20k, (B) Peg-35k, and (C) PEG-100k enhanced ESR sedimentation rates in whole blood.
Figure 6B:
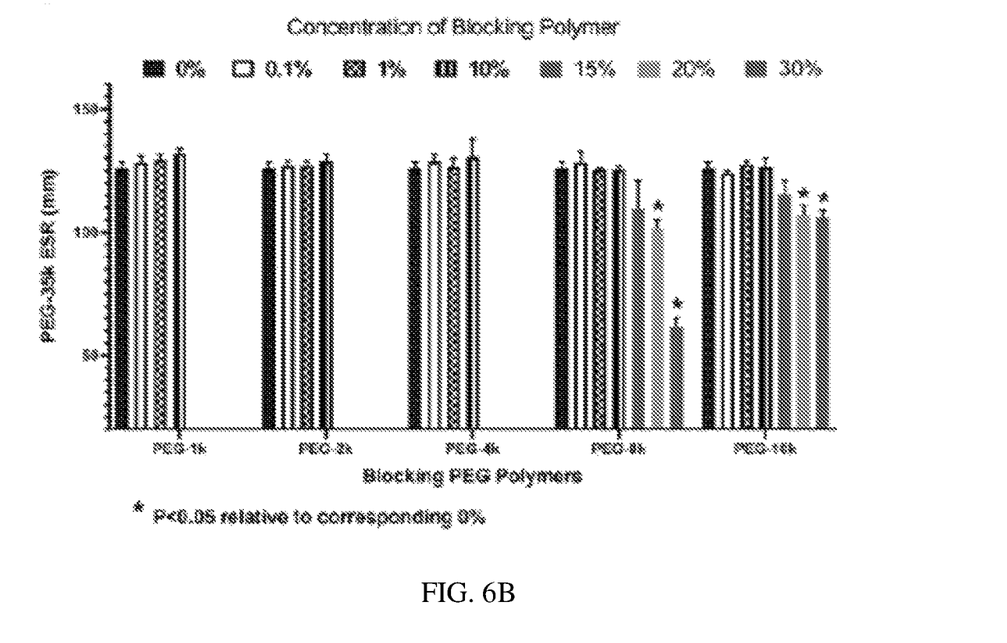
Figure 6C:
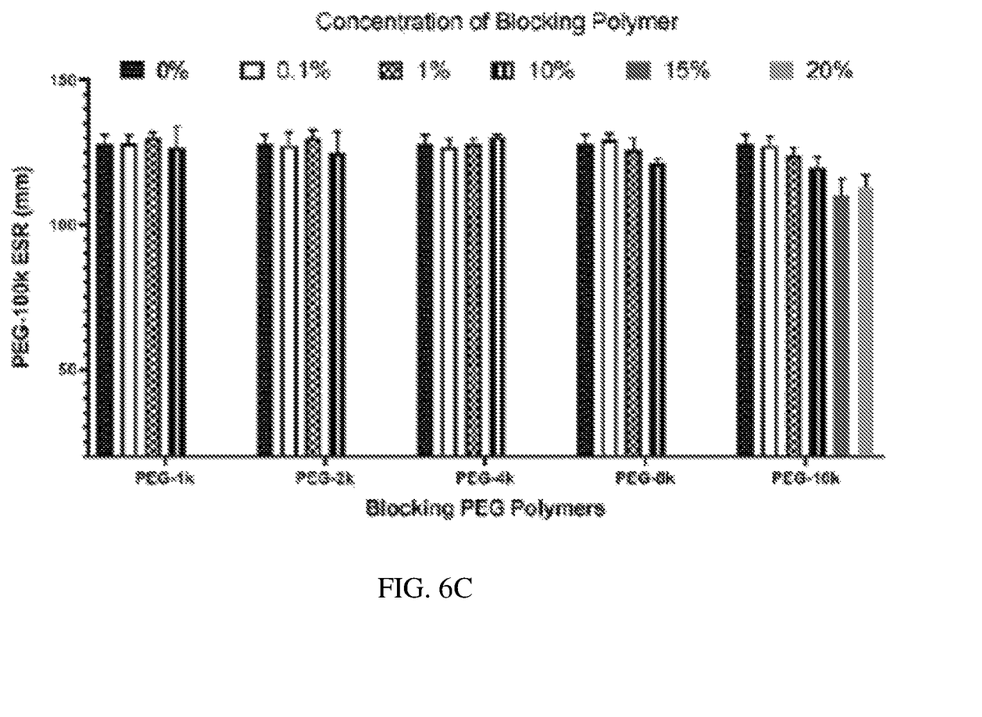

To test this hypothesis, we conducted systematic polymer blocking studies. Smaller PEG polymers with a molecular radius less than 4 nM (less than 10 kDa in molecular weight) were added back to the PEG treated whole blood in order to competitively interfere with PEG cross linking and ESR sedimentation. We tested three commercially available PEG polymers in the known therapeutic range shock (PEG-20k, PEG-35k, and PEG-100k). The results are in FIG. 6a-6c. We show much strong ESR effects (2×) with therapeutic concentrations of PEG-35k (FIG. 6b) and PEG-100k (FIG. 6c). The ability to inhibit these ESR effects using the smaller PEG polymers (PEG-1k to PEG-10k) are blunted as the molecular weight of the therapeutic PEG increases. Generally, it takes higher concentrations of the blocker PEG polymers to produce a lesser effect, relative to what is seen using PEG-20k.

Another advantage of using the smaller PEG polymers is the immuno-camouflage effects these polymers have on activated inflammatory cells. This serves to block and limit secondary resuscitation and reperfusion injury.

While the invention has been described in terms of its preferred embodiments, those skilled in the art will recognize that the invention can be practiced with modification within the spirit and scope of the appended claims. Accordingly, the present invention should not be limited to the embodiments as described above, but should further include all modifications and equivalents thereof within the spirit and scope of the description provided herein.

We claim:

1. An injectable composition, comprising:
   therapeutic polyethylene glycol with a molecular weight of from 18,000 Da to 40,000 Da at a concentration of from 5% w/v to 30% w/v;
   polyethylene glycol with a molecular weight of from 1,000 Da to 10,000 Da at a concentration of from 1% w/v to 30% w/v for inhibiting erythrocyte sedimentation associated with the therapeutic polyethylene glycol; and
   water,
   wherein the polyethylene glycol with a molecular weight of from 18,000 Da to 40,000 Da and the polyethylene glycol with a molecular weight of from 1,000 Da to 10,000 Da are dissolved in the water to provide a total volume of the composition ranging from 100 ml to 1000 ml; and
   the composition is configured to be delivered by injection.

2. The injectable composition of claim 1, wherein the polyethylene glycol with a molecular weight of from 1,000 to 10,000 Da is a polyethylene glycol with a molecular weight of 4,000 Da, 8,000 Da, or 10,000 Da.

3. The injectable composition of claim 1, wherein the polyethylene glycol with a molecular weight of from 1,000 Da to 10,000 Da is provided at a concentration of from 1% w/v to 10% w/v.

4. The injectable composition of claim 1, wherein the polyethylene glycol with a molecular weight of from 18,000 Da to 40,000 Da is a polyethylene glycol with a molecular weight of 18,000 Da, 20,000 Da, 25,000 Da, 30,000 Da, or 35,000 Da.

5. The injectable composition of claim 1, wherein the polyethylene glycol with a molecular weight of 18,000-40,000 Da is provided at a concentration of from 5% w/v to 20% w/v.

6. The injectable composition of claim 1, wherein the polyethylene glycol with a molecular weight of 18,000-40,000 Da is provided at a concentration of from 7.5% w/v to 10% w/v.

7. The injectable composition of claim 1, wherein the composition is configured to be delivered by intravenous injection.

8. The injectable composition of claim 1, comprising:
   a polyethylene glycol with a molecular weight of 20,000 Da, provided at a concentration of from 7.5% w/v to 10% w/v;
   a polyethylene glycol with a molecular weight of 4,000 Da, 8,000 Da or 10,000 Da, provided at a concentration of 1% w/v to 10% w/v; and
   water to provide a total volume of 136 ml to 680 ml.

9. The injectable composition of claim 1, wherein the water is deionized water.

10. The injectable composition of claim 1, wherein the composition further comprises one or more of sodium chloride, sodium lactate, potassium chloride, calcium chloride, and magnesium chloride.

11. An injectable infusion product, comprising:
    a bag configured for delivering fluid by injection; and
    an injectable composition of claim 1.

12. An injectable infusion product, comprising:
    a bag configured for delivering fluid by injection; and
    an injectable composition of claim 8.

13. A method for restoring or increasing local or global tissue perfusion in a subject in need thereof, wherein the subject suffers from reduced global or local tissue perfusion due to cardiogenic or noncardiogenic shock, comprising administering by injection to the subject a therapeutically effective amount of the injectable composition according to claim 1.

14. The method of claim 13, wherein the composition is administered intravenously.

15. The method of claim 13, further comprising a step of simultaneously or sequentially administering a cellular or acellular oxygen carrier solution.

16. The method of claim 15, wherein the acellular oxygen carrier solution is a hemoglobin based oxygen carrier (HBOC).

17. The method of claim 15, wherein the cellular oxygen carrier solution is whole blood or packed red blood cells.

18. The method of claim 15, wherein the amount of the cellular oxygen carrier solution administered is 50% or less of the estimated blood volume that would otherwise be needed in the absence of the composition.

19. The method of claim 15, wherein the cellular or acellular oxygen carrier solution is administered within 12 hours of administering the composition.

* * * * *